United States Patent [19]
Bowler

[11] 3,954,881
[45] May 4, 1976

[54] PROSTANOIC ACID DERIVATIVES

[75] Inventor: Jean Bowler, Macclesfield, England

[73] Assignee: Imperial Chemical Industries Limited, London, England

[22] Filed: July 15, 1974

[21] Appl. No.: 488,759

[30] Foreign Application Priority Data
Aug. 2, 1973 United Kingdom............... 36691/73

[52] U.S. Cl.......................... 260/613 D; 260/468 D; 260/210 R; 260/234 R; 260/611 R; 260/590 C; 424/180

[51] Int. Cl.²............................................ C07C 43/20

[58] Field of Search..................... 260/613 D, 590 C

[56] References Cited
UNITED STATES PATENTS 3,810,943    5/1974    Jones et al. ....................... 260/590 C

FOREIGN PATENTS OR APPLICATIONS 2,223,365    12/1972    Germany

*Primary Examiner*—James O. Thomas, Jr.
*Assistant Examiner*—G. Breitenstein
*Attorney, Agent, or Firm*—Cushman, Darby & Cushman

[57] ABSTRACT

The disclosure relates to novel ethers and glycosides of prostaglandin analogues, for example 16-(3-chlorophenoxy)-1-methoxy-17,18,19,20-tetranor-5-cis,13-trans-prostadien-9α,11α,15α-triol, to a process for their manufacture, to compositions containing them, and to their use in a method of inducing luteolysis in a warm-blooded animal host.

5 Claims, No Drawings

PROSTANOIC ACID DERIVATIVES

This invention relates to novel prostanoic acid derivatives which possess luteolytic and smooth muscle stimulant activity. The new compounds are therefore advantageous when used as contraceptives, for the induction of labour or termination of pregnancy, or for control of the oestrus cycle, and are also useful as hypotensives or for the relief of bronchospasm, and as inhibitors of blood platelet aggregation or of gastric secretion. The new compounds are also useful for addition to semen intended for artifical insemination of domestic animals, the success rate of insemination being thereby increased, especially in pigs and cattle.

According to the invention there is provided a prostanoic acid derivative of the formula:

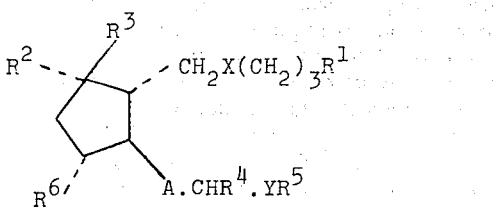

wherein $R^1$ is hydroxymethyl or carboxy radical, an alkoxycarbonyl radical of up to 11 carbon atoms, an alkoxymethyl radical of 2 to 7 carbon atoms, a glycopyranosyloxy-methyl radical, or a tetra-O-alkanoylglycopyranosyloxymethyl radical wherein each alkanoyl radical contains 1 to 4 carbon atoms; X is an ethylene or vinylene radical; $R^2$ is a hydroxy radical or an alkoxy or alkanoyloxy radical of 1 to 4 carbon atoms and $R^3$ is a hydrogen atom, and $R^2$ and $R^3$ together form an oxo radical; A is an ethylene or trans-vinylene radical; $R^4$ and $R^6$ which may be the same or different are each a hydroxy radical or an alkoxy radical of 1 to 4 carbon atoms; Y is a direct bond or an alkylene or alkyleneoxy radical of 1 to 5 carbon atoms, in the latter of which the carbon atom is bonded to the carbon atom of the —CHR⁴— group, and the oxygen atom is bonded to $R^5$; and $R^5$ is a phenyl or naphthyl radical which is unsubstituted or is substituted by halogen atoms, nitro, hydroxy or phenyl radicals, alkyl, alkenyl, halogenoalkyl, alkoxy or alkenyloxy radicals each of 1 to 4 carbon atoms, provided that when $R^1$ is a hydroxymethyl or carboxy radical, or an alkoxycarbonyl radical of up to 11 carbon atoms; at least one of $R^2$, $R^4$ and $R^6$ is an alkoxy radical; which compound bears 0 or 1 alkyl substituent of 1 to 4 carbon atoms on carbon atom 2, 3 or 4; and for those compounds wherein $R^1$ is a carboxy radical, the pharmaceutically or veterinarily acceptable base addition salts thereof.

A suitable value for $R^1$ when it is an alkoxycarbonyl radical of up to 11 carbon atoms is, for example, a methoxy-carbonyl, ethoxycarbonyl, n-butoxycarbonyl or n-decyloxy-carbonyl radical, particularly such an alkoxycarbonyl radical of up to 5 carbon atoms.

A suitable value for $R^1$ when it is an alkoxymethyl radical of 2 to 7 carbon atoms is, for example, a methoxymethyl, ethoxymethyl, propoxymethyl or butoxymethyl radical, particularly such an alkoxymethyl radical of up to 4 carbon atoms.

A suitable value for $R^1$ when it is a glycopyranosyloxymethyl radical is, for example, the D-form thereof, for example a D-glucopyranosyloxymethyl radical, and a suitable value for $R^1$ when it is a tetra-O-alkanoyl glycopyranosyloxymethyl radical is, for example, the D-form thereof, for example a tetra-O-acetyl-D-glycopyranosyloxymethyl radical, for example a tetra-O-acetyl-D-glucopyransyloxymethyl radical.

A suitable value for any one of $R^2$, $R^4$ and $R^6$ when it is an alkoxy radical of 1 to 4 carbon atoms is, for example, a methoxy, ethoxy, propoxy or butoxy radical, and a suitable value for $R^2$ when it is an alkanoyloxy radical is, for example, an acetoxy or propionyloxy radical.

Suitable halogen atom substituents in $R^5$ are, for example, chlorine, bromine or fluorine atoms, and especially a chlorine atom. Suitable alkyl, alkoxy, alkenyl or alkenyloxy substituents of 1 to 4 carbon atoms in $R^5$ are, for example methyl, t-butyl, allyl, methoxy or allyloxy radicals. Suitable halogenoalkyl substituents of 1 to 4 carbon atoms in $R^5$ are, for example, chloralkyl or fluoroalkyl radicals, for example trifluoromethyl radicals.

Suitable substituted aryl radicals are therefore, for example, chlorophenyl, chloronaphthyl, bromophenyl, fluorophenyl, tolyl, xylyl, methylnaphthyl, t-butylphenyl, methylchlorophenyl, trifluoromethylphenyl, hydroxyphenyl, methoxyphenyl, methoxynaphthyl, biphenylyl and tetrahydronaphthyl radicals.

Particular aryl radicals contain not more than two substituents and preferably only one substituent as defined above. Particular values for $R^5$ are, therefore, phenyl, 1-naphthyl, 2-naphthyl, 2-, 3- and 4-chlorophenyl, 4-bromophenyl, 2-, 3- and 4-fluorophenyl, 2,3-, 2,4-, 2,5-, 2,6-, 3,4- and 3,5-dichlorophenyl, 2-, 3- and 4-tolyl, 2,3-, 3,4- and 3,5-xylyl, 4-t-butylphenyl, 3-allylphenyl, 3- or 4-trifluoromethylphenyl, 4-hydroxyphenyl, 2-, 3- and 4-methoxyphenyl, 4-biphenylyl, 2-chloro-4-methylphenyl, 1-chloro-2-naphthyl, 4-chloro-2-naphthyl, 6-methyl-2-naphthyl, 6-methoxy-2-naphthyl and 5,6,7,8-tetrahydro-2-naphthyl radicals. Especially preferred aryl radicals are phenyl, 3- and 4-chlorophenyl and 3- and 4-trifluoromethylphenyl radicals, particularly the 3-chlorophenyl radical.

A suitable value for Y when it is an alkylene radical of 1 to 5 carbon atoms, or for the alkylene part of Y when it is an alkyleneoxy radical of 1 to 5 carbon atoms is, for example, an alkylene radical of 1 to 3 carbon atoms bearing 0, 1 or 2 alkyl substituents each of 1 to 3 carbon atoms, for example a methylene, ethylidene, isopropylidene, propylidene, 1-methylethylene, 1,1-dimethylethylene, 1-ethylethylene or 2-methylethylene radical, more especially a methylene, 1-methylethylene or isopropylidene radical.

Preferred values for Y are methyleneoxy, isopropylideneoxy and 1-methylethylene radicals.

A suitable value for the alkyl radical of up to 4 carbon atoms which may be present as a substituent on carbon atom 2, 3 or 4 is, for example the methyl radical.

Examples of pharmaceutically or veterinarily acceptable base-additions salts are the ammonium, alkylammonium containing 1 to 4 alkyl radicals each of 1 to 6 carbon atoms, alkanolammonium containing 1 to 3 2-hydroxy-ethyl radicals, and alkali metal salts, for example the triethylammonium, ethanolammonium, diethanolammonium, sodium and potassium salts.

It will be observed that the compounds of the formula I contain at least four asymmetric carbon atoms, namely carbon atoms 8, 11, 12 and 15, the relative configurations at three of which, 8, 11 and 12 are specified in formula I, and that carbon atoms 2, 3, 4, 9 and 16 may also be asymmetrically substituted, so that it is clear that such compounds can exist in optically active forms. It is to be understood that the useful properties of the racemate may be present to differing extents in the optical isomers, and that this invention relates to the racemic form of the compounds of formula I and any optically active form which shows the above useful properties, it being a matter of common general knowledge how the optically active forms may be obtained, and to determine their respective biological properties.

A preferred group of prostanoic acid derivatives of the invention comprises compounds of the formula I wherein $R^1$ is an alkoxymethyl radical, for example a methoxy-methyl radical, a D-glycopyranosyloxymethyl radical, for example a D-glucopyranosyloxymethyl radical, or a tetra-O-acetyl-D-glycopyranosyloxymethyl radical, for example a tetra-O-acetyl-D-glucopyranosyloxymethyl radical, X is a cis-vinylene radical, A is a trans-vinylene radical, $R^2$, $R^4$ and $R^6$ are hydroxy radicals, $R^5$ has any of the meanings defined above, and Y has any of the meanings defined above, but especially a methyleneoxy radical.

A further preferred group of prostanoic acid derivatives of the invention comprises compounds of the formula I wherein $R^1$ is a carboxy or alkoxycarbonyl radical as defined above, especially a methoxycarbonyl radical; $R^4$ is an alkoxy radical as defined above, for example a methoxy radical and $R^2$ and $R^6$ are hydroxy radicals; or $R^4$ and $R^6$ are each an alkoxy radical as defined above, for example a methoxy radical, and $R^2$ is a hydroxy radical or $R^2$ and $R^3$ together form an oxo radical; or $R^4$, $R^6$ and $R^2$ are each an alkoxy radical as defined above, for example a methoxy radical; X is a cis-vinylene radical; A is a trans-vinylene radical; Y has any of the meanings defined above but especially a methyleneoxy radical, and $R^5$ has any of the meanings defined above.

Preferred prostanoic acid derivatives of the invention are 16-(3-chlorophenoxy)-1-methoxy-17,18,19,20-tetranor-5-cis,13-trans-prostadien-9α,11α,15α-triol, 1-butoxy-16-(3-chlorophenoxy)-17,18,19,20-tetranor-5-cis,13-trans-prostadien-9α,11α,15α-triol, 16-(3-chlorophenoxy)-9α,11α-dihydroxy-15α-methoxy-17,18,19,20-tetranor-5-cis,13-trans-prostanoic acid, 16-(3-chlorophenoxy)-1-D-glucopyranosyloxy-17,18,19,20-tetranor-5-cis,13-trans-prostadien-9α,11α, 15α-triol, 16-(3-chlorophenoxy)-1-(2,3,4,6-tetra-O-acetyl-D-glucopyranosyloxy)-17,18,19,20-tetranor-5-cis,13-trans-prostadien-9α,11α,15α-triol, methyl 16-(3-chlorophenoxy)-9α-hydroxy-11α,15α-dimethoxy-17,18,19,20-tetranor-5-cis,13-trans-prostadienoate, methyl 16-(3-chlorophenoxy)-11α,15α-dimethoxy-9-oxo-17,18,19,20-tetranor-5-cis,13-trans-prostadienoate and methyl 16-(3-chlorophenoxy)-9α,11α,15α-trimethoxy-17,18,19,20-tetranor-5cis,13-trans-prostadienoate.

The new prostanoic acid derivatives of the invention may be manufactured by methods known in themselves for the manufacture of chemically analogous compounds. Thus, the following processes, wherein $R^1$, $R^2$, $R^3$, $R^5$, A, X and Y have the meanings given above unless otherwise defined, are provided as further features of the invention:

a. for those compounds wherein $R^1$ is a carboxy, alkoxymethyl, glycopyranosyloxymethyl or tetra-O-alkanoyl glycopyranosyloxymethyl radical, $R^2$, $R^4$ and $R^6$ are hydroxy radicals and Y is an alkylene or alkyleneoxy radical, the hydrolysis of a compound of the formula:

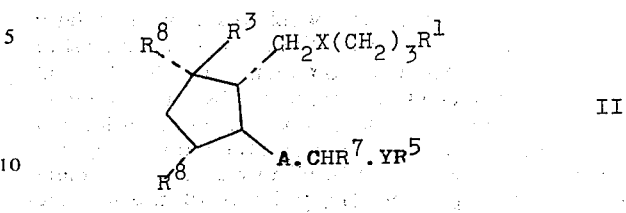

or, when $R^1$ is carboxy, of a mixed anhydride thereof, wherein $R^1$ has the meaning defined immediately above, $R^7$ is an alkoxy radical of 1 to 4 carbon atoms or a tetrahydropyran-2-yloxy radical, and $R^8$ is a tetrahydropyran-2-yloxy radical, and bearing 0 or 1 alkyl substituent of 1 to 4 carbon atoms on carbon atom 2, 3 or 4, whereafter if a salt of a compound wherein $R^1$ is a carboxyl group is required, a carboxylic acid so obtained is reacted with a base; or b. for those compounds where $R^1$ is an alkoxycarbonyl radical, the reaction of a carboxylic acid derivative of the formula I, wherein $R^1$ is a carboxy radical, with a diazoalkane of up to 10 carbon atoms, or of a salt thereof, for example the silver salt, with an alkyl halide, for example an alkyl iodide; or c. for those compounds wherein $R^1$ is an alkoxycarbonyl radical, the reaction of a compound of the formula II, wherein $R^1$ is a carboxy radical, $R^7$ is an alkoxy radical, and $R^8$ is a tetrahydropyran-2-yloxy radical, with an alkanol of 1 to 10 carbon atoms in the presence of a strong acid, for example toluene-p-sulphonic acid, whereafter if the corresponding carboxylic acid is required, the ester so obtained is hydrolysed, for example with potassium hydroxide; or d. for those compounds wherein $R^1$ is a hydroxymethyl radical, the reduction of an ester, of the formula I wherein $R^1$ is an alkoxycarbonyl radical, for example an alkoxycarbonyl radical of up to 11 carbon atoms, with a complex metal hydride, for example lithium aluminium hydride; or e. for those compounds wherein $R^1$ is a carboxy radical, $R^2$ is a hydroxy radical and $R^3$ is a hydrogen atom, and Y is a direct bond, the reaction of a lactol of the formula:

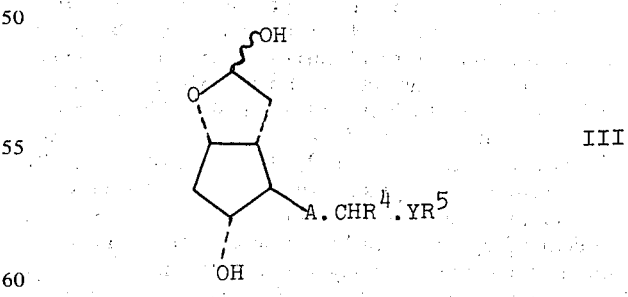

wherein $R^4$ is an alkoxy radical, with a (4-carboxybutyl)-triphenylphosphonium salt, for example the bromide, bearing 0 or 1 alkyl substituent of 1 to 4 carbon atoms on the trimethylene group thereof, in the presence of a strong base, whereafter if a salt is required the product so obtained is reacted with a base; or f. for those compounds wherein $R^4$ is a hydroxy radical, the reduction of a compound of the formula:

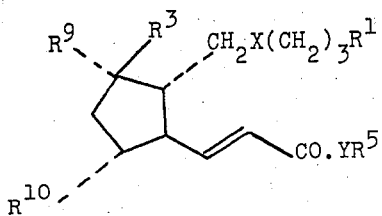

wherein $R^1$ is an alkoxymethyl, glycopyranosyloxymethyl or tetra-O-alkanoyl glycopyranosyloxymethyl radical, and $R^9$ and $R^{10}$ are each a hydroxy or protected hydroxy radical, and which bears 0 or 1 alkyl substituent of 1 to 4 carbon atoms on carbon atom 2, 3 or 4, whereafter when $R^9$ and $R^{10}$ are each a protected hydroxy radical the protecting groups are removed; or g. for those compounds wherein X is the trans-vinylene radical, the separation of a mixture comprising the compound of the formula I wherein X is the cis-vinylene radical; and the compound of the formula I wherein X is the trans-vinylene radical; or h. for those compounds wherein $R^1$ is an alkoxycarbonyl radical and $R^4$, or $R^4$ and $R^6$, or $R^4$, $R^6$ and $R^2$ are alkoxy radicals, the reaction of an ester of the formula I wherein $R^1$ is an alkoxycarbonyl radical and $R^2$, $R^4$ and $R^6$ are hydroxy radicals, with an alkyl halide, for example an iodide or bromide, in the presence of respectively one, two or three equivalents of a strong base, for example sodium hydride; or i. for those compounds wherein $R^1$ is a glycopyranosyloxymethyl radical, the hydrolysis of the corresponding compound of the formula I wherein $R^1$ is a tetra-O-alkanoylglycopyranosyloxymethyl radical, for example with alcoholic potassium hydroxide; or j. for those compounds wherein $R^2$ and $R^3$ together form an oxo radical, and $R^4$ and $R^6$ are each an alkoxy radical, the oxidation, for example with Jones' reagent, of the corresponding compound of the formula I wherein $R^2$ is a hydroxy radical and $R^3$ is a hydrogen atom.

In process (a), a suitable mixed anhydride is a mixed anhydride with a lower alkanoic acid, for example a lower alkanoic acid of up to 8 carbon atoms, for example acetic acid.

The hydrolysis in process (a) may be carried out under acidic conditions, for example in aqueous acetic acid, and it may be carried out at ambient temperature or at an elevated temperature of up to 60°C.

In process (e), the strong base may be a sodium base, for example methanesulphinylmethyl sodium, leading to a product of the formula I wherein X is the cis-vinylene radical, or it may be a lithium base, for example n-butyl-lithium, in sulpholane as solvent, leading to a mixture of products of the formula I wherein X is the cis- or trans-vinylene radical, from which the trans-isomer may be isolated by process (g).

In process (f), the reduction may be carried out, for example, with aluminium tri-isopropoxide or di-isobornyloxy aluminium isopropoxide to give a compound of the formula I wherein A is a trans-vinylene radical, or with, for example, sodium borohyride to give a compound of the formula I wherein A is an ethylene radical, if necessary after removal of protecting groups $R^9$ and $R^{10}$.

In (g), (g), a suitable method for the separation of a trans-vinylene compound of the invention from a mixture of trans-vinylene and cis-vinylene compounds is by chromatography of the mixture on silica gel impregnated with silver nitrate, but other conventional methods of separating cis-trans mixtures may also be used, for example fractional crystallization.

In process (h), it will be understood that, if all trace of moisture is not excluded from the reactants, then a mixture of products will result, for example when using three equivalents of base, a mixture of dialkoxy and trialkoxy products may be obtained, but such a mixture can, of course, be separated in conventional manner, for example by chromatography.

Starting materials of the formula II wherein X is a cis-vinylene radical may be obtained as follows:

a. The starting material of the formula II wherein $R^1$ is alkoxycarbonyl and $R^7$ is alkoxy, used in process (a) of the invention may be obtained from the corresponding known compounds of the formula I, wherein $R^1$ is alkoxycarbonyl and $R^4$ is hydroxy, by selective alkylation thereof with an alkyl halide, for example an alkyl iodide in a solvent, for example dimethoxyethane, in the presence of one equivalent of a strong base such as sodium hydride. Such a compound may be hydrolysed, under either acidic or basic conditions, to give a starting material of the formula II wherein $R^1$ is the carboxy radical, but it will be understood that the hydrolysis of the tetrahydropyran-2-yl radical $R^6$, which is the process (a) of the invention, may occur simultaneously. Also, the starting material II wherein $R^1$ is an alkoxycarbonyl radical may be reduced, for example with lithium aluminium hydride, to the corresponding starting material of the formula II wherein $R^1$ is a hydroxymethyl radical, which may in turn be reacted with an alkyl halide in a solvent such as dimethoxyethane in the presence of a strong base, for example sodium hydride, to give a starting material of the formula II wherein $R^1$ is an alkoxymethyl radical, or it may be reacted with a suitable glycopyranosyl halide, for example the bromide, in the presence of silver oxide, to give a starting material of the formula II wherein $R^1$ is a tetra-O-alkanoyl glycopyranosyloxymethyl radical, hydrolysis of which gives the starting material of the formula II wherein $R^1$ is a glycopyranosyloxymethyl radical.

b. The starting material of the formula II wherein $R^1$ is a glycopyranosyloxymethyl or tetra-O-alkanoyl glycopyranosyloxymethyl radical and $R^4$ is a hydroxy radical, may be obtained from the corresponding known compound of the formula II wherein $R^1$ is a hydroxymethyl radical by reaction thereof with a suitable tetra-O-alkanoyl glycopyranosyl halide, for example the bromide, in the presence of silver oxide, whereafter the protecting alkanoyl radicals may, if desired, be removed by hydrolysis.

Starting materials of the formula II wherein X is an ethylene radical may be obtained by hydrogenation of a suitable intermediate wherein X is a cis-vinylene radical.

The starting material of the formula II wherein X is a trans-vinylene radical may be prepared by separating the mixture of cis and trans isomers obtained by reacting a known lactol of the formula:

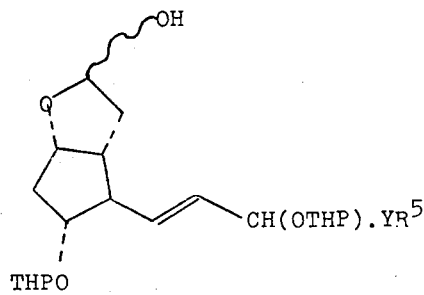

V wherein Y and $R^5$ are defined above and THP represents the tetrahydropyran-2-yl radical, with (4-carboxybutyl)-triphenyl phosphonium bromide in the presence of n-butyl-lithium, and subsequently hydrolysing the protecting tetrahydropyranyl radicals. The trans compound thus obtained, wherein $R^1$ is a carboxy radical, may be converted by conventional means to corresponding compounds wherein $R^1$, $R^7$ and $R^8$ have any of the other meanings defined above.

The starting material of the formula III used in the process (e) of the invention may be obtained by reacting the known aldehyde VI with a compound $(CH_3O)_2$.$PO.CH_2.COYR^5$ or a phosphorane $Ph_3P:CH.COYR^5$, in the presence of a strong base, to give an unsaturated ketone VII which is reduced to the enol VIII. The enol VIII is alkylated with an alkyl halide, for example an alkyl iodide, in a solvent such as dimethoxyethane in the presence of one equivalent of a strong base, for example sodium hydride, to give the ether IX. The ether IX is hydrolysed to the alcohol X, which is then reduced, for example with di-isobutyl aluminium hydride, to give the required lactol starting material III, wherein A is a trans-vinylene radical.

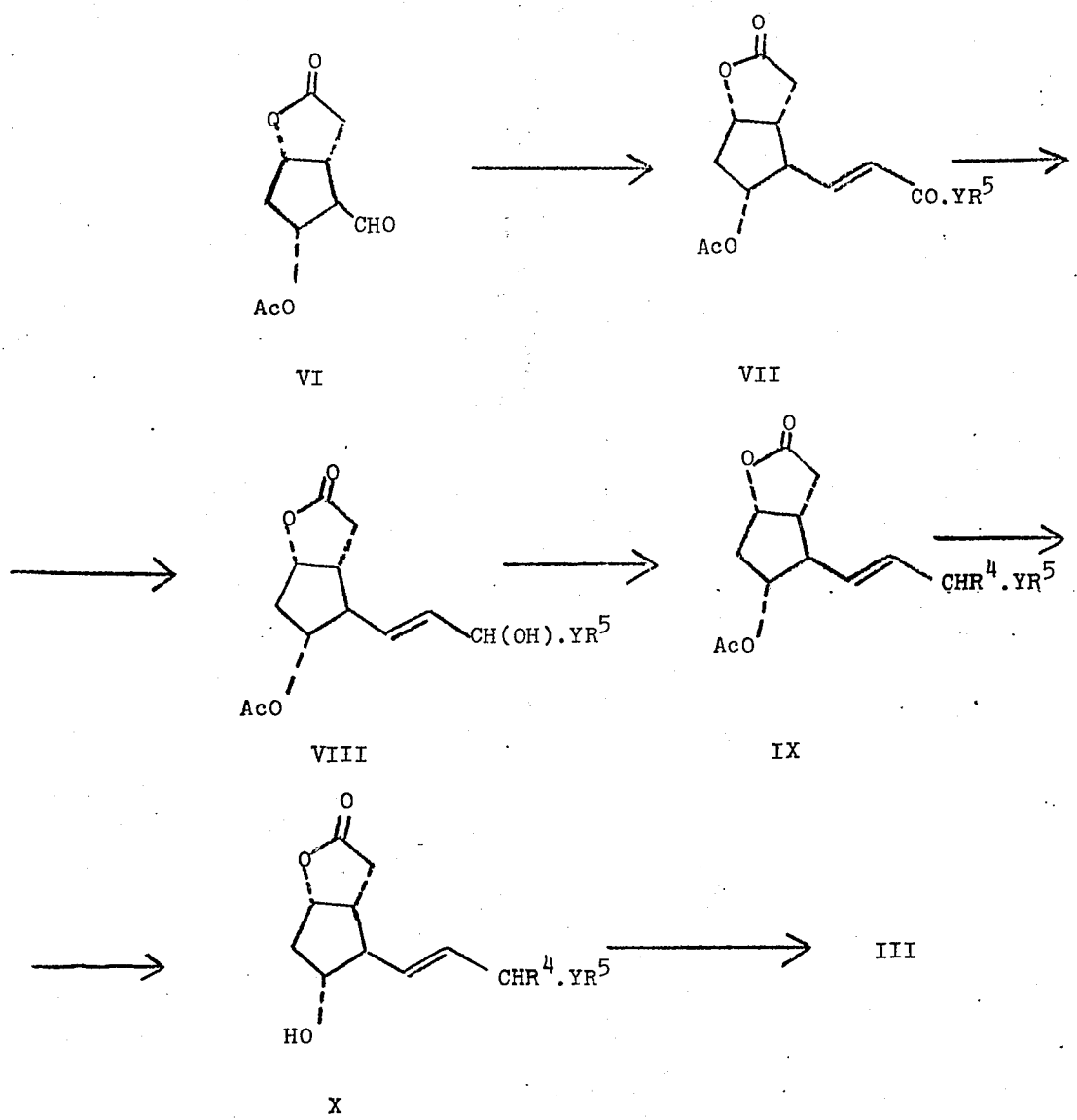

Ac represents the acetyl or 4-phenylbenzoyl radical.

The lactol starting material III, wherein A is an ethylene radical, may be obtained by hydrogenating an unsaturated ketone VI, in the presence of a palladium-on-carbon catalyst, to give a saturated ketone which is then used in place of the unsaturated ketone VI in the above-described reaction sequence.

The enone starting material IV may be prepared as follows:

4β-Dimethoxymethyl-2,3,3aβ,6aβ-tetrahydro-5α-hydroxy-6β-iodo-2-oxocyclopenteno[b]furan (XI) is treated with tributyl tin hydride to give the deiodinated lactone XII. The 5α-hydroxy group is protected as the tetrahydropyran-2-yl ether XIII, the lactone is reduced to the lactol XIV, using di-isobutyl aluminium hydride, and the lactol is reacted with (4-carboxybutyl)triphenylphosphonium bromide to give the cyclopentanol derivative XV, which on methanolysis forms a methyl ester with concomitant hydrolysis of the tetrahydropyranyl ether group XVI ($R^9 = R^{10} = H$). The hydroxy radicals are reprotected as tetrahydropyranyl groups (XVI, $R^9 = R^{10} = THP$) and the ester is reduced with lithium aluminium hydride to the alcohol XVII ($R^{11} = H$), which may if required be converted to the corresponding alkoxymethyl, glycopyranosyloxymethyl or tetra-O-alkanoyl glycopyranosyloxymethyl group. The acetal group is then hydrolysed to the aldehyde XVIII, which is reacted with a phosphonate $(CH_3O)_2PO.CH_2CO.YR^5$

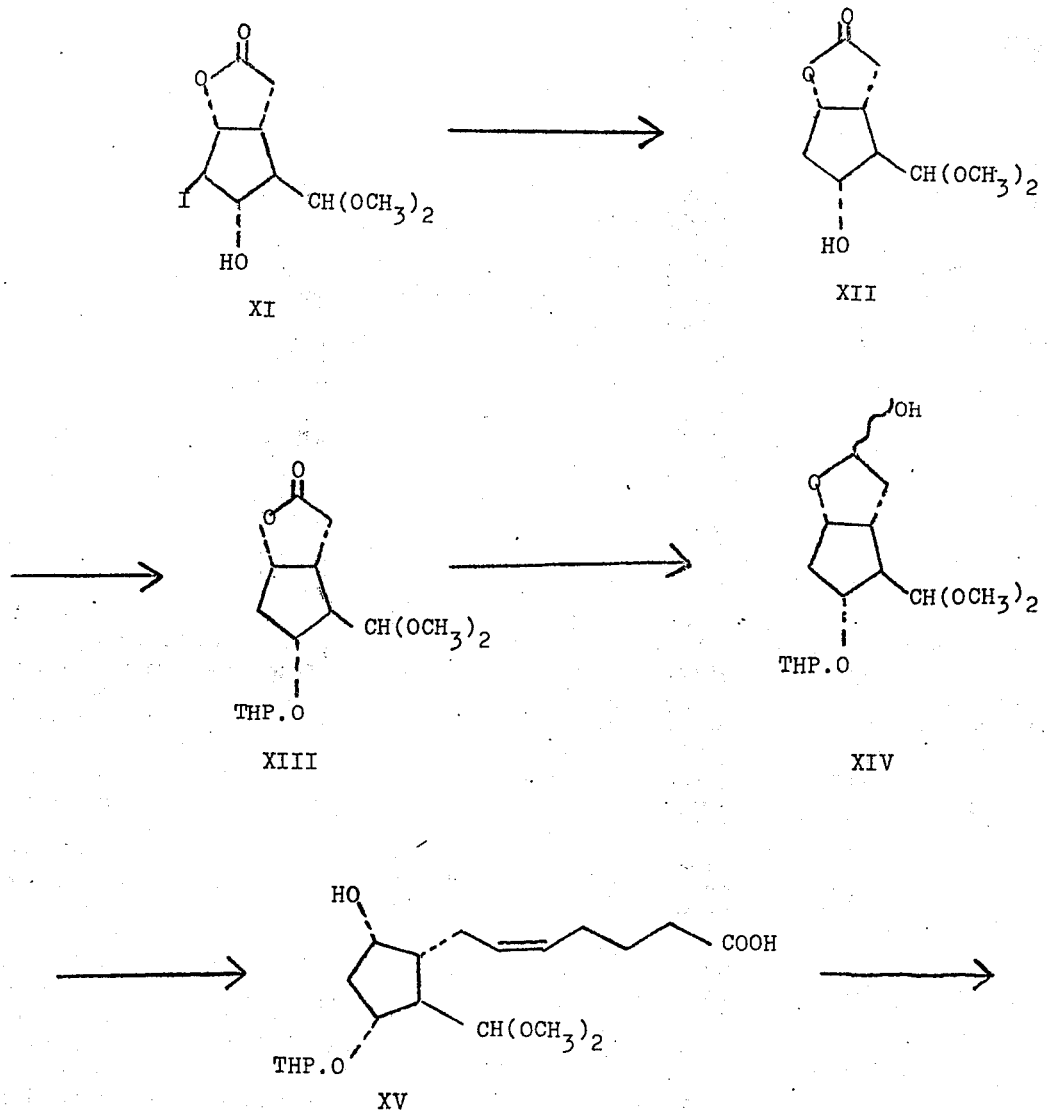

THP = tetrahydropyran-2-yl

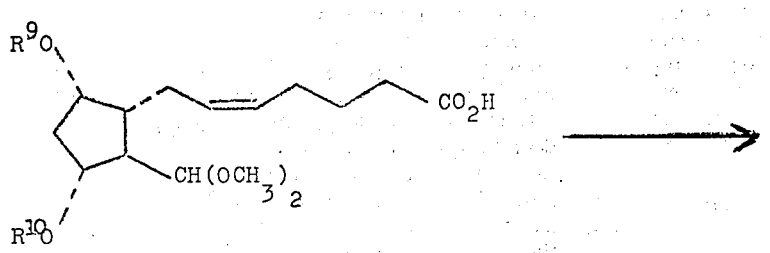

XVI

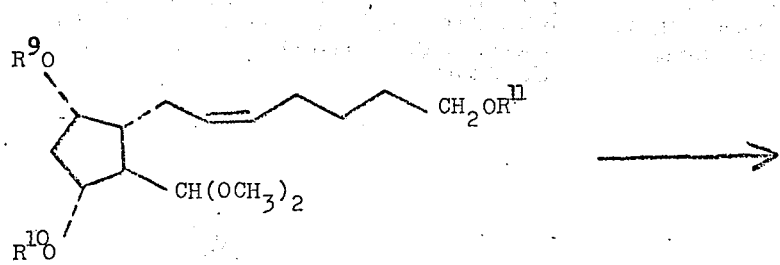

XVII

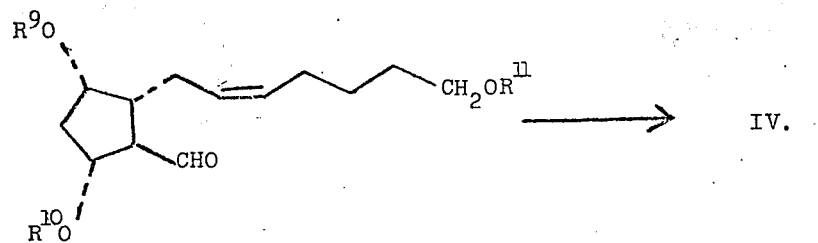

XVIII in the presence of a strong base to give the required enone IV. borohydride The mixture of cis and trans isomers, wherein Y is an alkylene or methyleneoxy radical, from which the trans isomer may be separated in the process (i) of the invention may be obtained, for example, by reacting a known lactol of the formula:

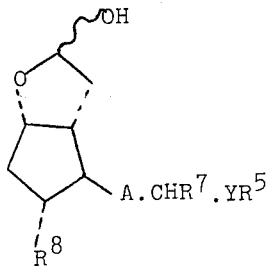

XIX wherein $R^5$, $R^7$, $R^8$ and A have the meanings defined above, with the ylide generated from a (4-carboxybutyl)-triphenylphosphonium salt, for example the bromide, by butyl-lithium in a solvent, for example sulpholane, and hydrolysing the protecting groups $R^7$ and $R^8$ from the product thus obtained.

It is, of course, to be understood that an optically active compound of the invention may be obtained either by resolving the corresponding racemate, or by carrying out the above-described reaction sequence starting from an optically active intermediate, for example from an optically active aldehyde of the formula VI(Ac = acetyl or p-phenyl-benzoyl).

As stated above, the compounds of the invention possess luteolytic properties. For example, 16-(3-chlorophenoxy)-1-methoxy-17,18,19,20-tetranor-5-cis,13-trans-prostadien-9α,11α,15α-triol is approximately 200 times more active than prostaglandin $F_2α$ in a luteolytic test in the hamster, (oral dosing), but has only one twentieth the smooth muscle stimulant activity of prostaglandin $F_2α$. No indication of toxicity has been noted at luteolytically effective doses.

The compounds of the invention are therefore useful, for example, for the induction of labour in childbirth, and for this purpose are used in the same way as it is known to use the naturally-occurring prostaglandins $E_1$ and $E_2$, that is to say, by administering a sterile, substantially aqueous solution containing from 0.01 to 10µg./ml., preferably 0.01 to 1µg./ml. of active compound, by intravenous, extraovular or intra-amniotic administration until labour commences. Also, for this purpose, the compounds of the invention may be used in combination, or concurrently, with a uterine stimulant, for example oxytocin, in the same way that it is known to use prostaglandin $F_2\alpha$ in combination, or concurrently, with oxytocin for the induction of labour.

When a compound of the invention is to be used for the control of the oestrus cycle in animals, it may be used in combination, or concurrently, with a gonadotrophin, for example PMSG (pregnant mare serum gonadotrophin) or HCG (human chorionic gonadotrophin) to hasten the onset of the next cycle.

Thus, according to a further feature of the invention there is provided a pharmaceutical or veterinary composition comprising a cyclopentane derivative of the invention, together with a pharmaceutically or veterinarily acceptable diluent or carrier.

The composition may be in the form suitable for oral administration, for example tablets or capsules, in a form suitable for inhalation, for example an aerosol or a solution suitable for spraying, in a form suitable for parenteral administration, for example sterile injectable aqueous or oily solutions or suspensions, or in the form of a suppository, suitable for anal or vaginal use.

The compositions of the invention may be prepared by conventional means, and may incorporate conventional excipients.

The invention is illustrated, but not limited by the following Examples.

EXAMPLE 1

A solution of 16-(3-chlorophenoxy)-1-methoxy-9α,11α,15α-tris(tetrahydropyran-2-yloxy)-17,18,19,20-tetranor-5-cis,13-trans-prostadiene (50mg.) in a 2:1 mixture of acetic acid and water (2ml.) was stirred at 40°C. for 4 hours. The solvents were evaporated and the residue was chromatographed on thin layer chromatography plates supplied commercially by Merck of Darmstadt, using 3% acetic acid in ethyl acetate as the developing solvent, to give 16-(3-chlorophenoxy)-1-methoxy-17,18,19,20-tetranor-5-cis,13-trans-prostadien-9α,11α, 15α-triol as a clear oil, $R_F = 0.5$. Measurement of the mass spectrum of the tris(trimethylsilyl)derivative gave $M^+ = 640.3159$ (calculated for $C_{32}H_{57}ClO_5Si_3 = 640.3202$). The tris(tetrahydropyranyl ether) used as starting material may be prepared as follows:

To a solution of methyl 16-(3-chlorophenoxy)-9α,11α, 15α-trihydroxy-17,18,19,20-tetranor-5-cis,13-trans-prostdienoate (150mg.) in methylene chloride (3ml.), under an atmosphere of nitrogen, were added successively redistilled 2,3-dihydropyran(1ml.) and a solution of anhydrous toluene-p-sulphonic acid in tetrahydrofuran (0.1ml. of a 1% solution). After 10 minutes, pyridine (3 drops) was added, followed by ethyl acetate (50ml.). The solution was washed successively with saturated sodium bicarbonate solution and saturated brine, and was dried. Evaporation of the solvents gave the tris(tetrahydropyranyl ether) as a clear oil, $R_F = 0.7$ (50% ethyl acetate in toluene).

A solution of the tris(tetrahydropyranyl ether), (120mg.) in dry ether (5ml.) was added to a suspension of lithium aluminium hydride (50mg.) in ether (5ml.). The mixture was stirred at room temperature for 2 hours, the excess of hydride was destroyed by the addition of water (1ml.) and the mixture was extracted with ethyl acetate to give 16-(3-chlorophenoxy)-9α,11α,1-5α-tris(tetrahydropyran-2-yloxy)-17,18,19,20-tetranor-5-cis,13-trans-prostadien-1-ol, $R_F = 0.4$ (50% ethyl acetate in toluene).

To a solution of 1-alcohol (50mg.) in dimethoxyethane (1ml.) were added successively methyl iodide (0.5ml.) and sodium hydride (4mg. of a 60% suspension in oil). The mixture was stirred at room temperature for 18 hours, the solvents were removed under reduced pressure, and the residue was shaken with a mixture of ethyl acetate (10mls.) and water (2mls.). The organic phase was separated and dried, and the solvent was evaporated to give the required tris(tetrahydropyranyl ether), $R_F = 0.7$ (ethyl acetate).

EXAMPLE 2

The process described in the first part of Example 1 was repeated, using the corresponding 1-butoxy tris(tetrahydropyranyl ether) in place of the 1-methoxy compound, to give 1-butoxy-16-(3-chlorophenoxy)-17,18,19,20-tetranor-5-cis,13-trans-prostadien-9α,1-1α,15α-triol, $R_F = 0.7$ (3% acetate acid in ethyl acetate). The mass spectrum of the tris(trimethylsilyl) derivaive showed = 682.3630 (calculated for $C_{35}H_{63}ClO_5Si_3 = 682.3671$).

The 1-butoxy tris(tetrahydropyranyl ether) starting material may be obtained by the process described in the second part of Example 1, using butyl iodide in place of methyl iodide.

EXAMPLE 3

To a solution of 16-(3-chlorophenoxy)-9α,11α,15α-trihydroxy-17,18,19,20-tetranor-5-cis, 13-trans-prostadienol (23mg.) in methylene chloride (3ml.) were added successively anhydrous calcium sulphate (−10 mesh) (50mg.) freshly prepared silver oxide (30mg.) and 2,3,4,6-tetra-O-acetylglucopyranosyl bromide (30mg.). The mixture was stirred at room temperature overnight, and was filtered. The filtrate was evaporated to dryness to give a crude product, which was purified by thin layer chromatography on silica gel plates, using ethyl acetate as the developing solvent, to give 16-(3-chlorophenoxy)-1-(2,3,4,6-tetra-O-acetyl-D-glucopyranosyloxy)-17,18,19,20-tetranor-5-cis, 13-trans-prostadien-9α,11α,15α-triol, $R_F = 0.4$ (ethyl acetate). The n.m.r. spectrum in deuterated acetone showed the following characteristic bands (δ values):

6.9–7.4, multiplet, 4 aromatic protons.
5.4–5.8, broad multiplet, 4 olefinic protons.
3.5–5.1, broad multiplets, 17 protons next to oxygen.
The mass spectrum of the tris(trimethylsilyl)derivative showed $(M—C_6H_4Cl.OCH_2)^+ = 815.3955$ (calculated for $C_{38}H_{67}O_{13}Si_3 = 815.3889$).

EXAMPLE 4

To a solution 16-(3-chlorophenoxy)-1-(2,3,4,6-tetra-O-acetyl-D-glucopyranosyloxy)-17,18,19,20-tetranor-5-cis,13-trans-prostadien-9α,11α,15α-triol (20mg.) in methanol (1ml.) was added potassium hydroxide (0.2ml. of a molar solution in methanol). The mixture was stirred at room temperature for 18 hours, the pH was adjusted to 7 with acetic acid, the solvent was evaporated and the residue was dried by azeotropic distillation. The residue was chromatographed on thin layer plates using a mixture of 70% n-propanol, 10% ethyl acetate and 20% water as eluant, followed by a second development with 10% water in acetonitrile, to give 16-(3-chlorophenoxy)-1-D-glucopyranosyloxy-17,18,19,20-tetranor-5-cis, 13-trans-prostadien-9α,1-1α,15α-triol. The n.m.r. spectrum in deuterated methanol showed the following characteristic bands (δ values):
  6.9–7.2, 4 aromatic protons
  5.3–5.8, 4 olefinic protons.

EXAMPLE 5

To a solution of methyl 16-(3-chlorophenoxy)-9α,1-1α,15α-trihydroxy-17,18,19,20-tetranor-5-cis, 13-trans-prostadienoate (40mg.) in dimethoxyethane (1ml.) were added successively methyl iodide (0.5ml.) and sodium hydride (4mg. of a 60% suspension in oil). The mixture was stirred at room temperature for 1 hour. The solvents were evaporated under reduced pressure, and the residue was shaken with a mixture of ethyl acetate (10ml.) and water (2ml.). The organic phase was separated and dried, the solvent was evaporated, and the residue was purified by thin layer chromatography on silica gel plates using ethyl acetate as the developing solvent, to give methyl 16-(3-chlorophenoxy)-9α,11α-dihydroxy-15α-methoxy-17,18,19,20-tetranor-5-cis, 13-trans-prostadienoate, $R_F$ = 0.5 (ethyl acetate). The n.m.r. spectrum showed the following characteristic bands (δ values):
  6.9–7.2, 4 aromatic protons
  5.3–5.6, 4 olefinic protons
  3.95, 2H, singlet, —C$\underline{H}_2$—O—
  3.61, 3H, singlet, —CO$_2$$\underline{Me}$
  3.35, 3H, singlet, —OC$\underline{H}_3$

EXAMPLE 6

To a solution of methyl 16-(3-chlorophenoxy)-9α,1-1α-dihydroxy-15α-methoxy-17,18,19,20-tetranor-5-cis, 13-trans-prostadienoate (11mg.) in a mixture of methanol (1ml.) and water (0.5ml.) was added M potassium hydroxide solution (1ml.). The mixture was stirred at room temperature for 4 hours and neutralised with acetic acid, and the organic solvents were evaporated under reduced pressure. The aqueous residue was adjusted to pH 3 with aqueous oxalic acid, and extracted with ethyl acetate. The extract was dried, the solvent was evaporated, to give 16-(3-chlorophenoxy)-9α,11α-dihydroxy-15α-methoxy-17,18,19,20-tetranor-5-cis, 13-trans-prostadienoic acid, $R_F$ = 0.4 (3% acetic acid in ethyl acetate). The n.m.r. spectrum showed the following characteristic bands (δ values):
  6.9–7.3, 4 aromatic protons.
  5.3–5.6, 4 olefinic protons.
  3.35, 3H, singlet, methoxy.
The mass spectrum of the tris(trimethylsilyl) derivative showed M$^+$ = 654.2974 (calculated for $C_{32}H_{55}ClSi_3O_6$ = 654.2995).

EXAMPLE 7

To a solution of methyl 16-(3-chlorophenoxy)-9α,1-1α,15α-trihydroxy-17,18,19,20-tetranor-5-cis,13-trans-prostadienoate (40mg.) in 1,2-dimethoxyethane (1ml.) were added successively sodium hydride (12mg. of a 60% suspension in oil) and methyl iodide (0.5ml.), and the mixture was stirred at room temperature for 2 hours. The solvents were evaporated under reduced pressure, and the residue was shaken with a mixture of ethyl acetate (10ml.) and water (2ml.). The organic phase was separated and dried, the solvent was evaporated, and the residue was purified by thin layer chromatography on silica gel plates, using 50% ethyl acetate in toluene as the developing solvent to give:
  methyl 16-(3-chlorophenoxy)-9α-hydroxy-11α,15α-dimethoxy-17,18,19,20-tetranor-5-cis, 13-trans-prostadienoate, $R_F$ = 0.3 (50% ethyl acetate in toluene).
The n.m.r. spectrum in deuterated chloroform showed the following characteristic bands (δ values):
  6.8–7.2, multiplet, 4 aromatic protons
  5.3–5.7, broad multiplet, 4 olefinic protons
  3.65, singlet, 3H, methyl ester
  3.32 and 3.38, singlets, 6H, methyl esters.
The mass spectrum of the trimethylsilyl ether showed M$^+$ = 538.2492 (calculated for $C_{28}H_{43}O_6ClSi$ = 538.2517)
  and methyl 16-(3-chlorophenoxy)-9α,11α,15α-trimethoxy-17,18,19,20-tetranor-5-cis, 13-trans-prostadienoate, $R_F$ = 0.5 (50% ethyl acetate in toluene). The n.m.r. spectrum in deuterated chloroform showed the following characteristic bands (δ values):
  6.8–7.2, multiplet, 4 aromatic protons
  5.3–5.7, broad multiplet, 4 olefinic protons
  3.65, singlet, 3H, methyl ester
  3.25, 3.32 and 3.38, singlets, 9H, methyl ethers
The mass spectrum showed (M-Cl.C$_6$H$_4$.OCH$_2$)$^+$ = 339.2171 (calculated for $C_{19}H_{31}O_5$ = 339.2145).

EXAMPLE 8

To a solution of methyl 16-(3-chlorophenoxy)-9-hydroxy-11α,15α-dimethoxy-17,18,19,20-tetranor-5-cis, 13-trans-prostadienoate (26mg.) in acetone (1ml.) at −10°C. was added Jones' reagent (chromic acid in acetone) (25μl.). After 15 minutes, isopropanol (1 drop) was added, followed by ethyl acetate (20mls.). The solution was washed with 1:1 saturated brine/water and was dried. Evaporation of the solvents and purification of the residue by thin-layer chromatography on silica gel plates using ethyl acetate as the developing solvent gave methyl 16-(3-chlorophenoxy)-11α,15α-dimethoxy-9-oxo-17,18,19,20-tetranor-5-cis,13-trans-prostadienoate, $R_F$ = 0.75 (50% ethyl acetate in toluene). The n.m.r. spectrum in deuterated acetone showed the following characteristic bands (δ values):
  6.9–7.3, multiplet, 4 aromatic protons
  5.2–6.0, broad multiplet, 4 olefinic protons
  3.58, singlet, 3H, methyl ester
  3.33 and 3.35, singlets, 6H, methyl ethers.
The mass spectrum of methoxime derivative showed M$^+$ = 493.2210 (calculated for $C_{26}H_{36}NO_6Cl$ = 493.2230).

EXAMPLE 9

|  | % w/v |
| --- | --- |
| 16-(3-Chlorophenoxy)-1-methoxy-17,18,19,20-tetranor-5-cis,13-trans-prostadien-9α,11α,15α-triol | 0.003 |
| Sodium phosphate B.P. | 2.90 |
| Sodium acid phosphate B.P. | 0.30 |
| Water for injection | to 100 |

The sodium phosphate B.P. was dissolved in about 80% of water, followed by the prostadienoic acid derivative, and when dissolved, the sodium acid phosphate B.P. The solution was made up to volume with water for injection, and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration by intravenous infusion.

The prostadienoic acid derivative may, of course, be replaced by an equivalent amount of another prostanoic acid derivative of the invention.

EXAMPLE 10

The process described in Example 9 was repeated, omitting the sodium phosphate B.P. and sodium acid phosphate B.P., to give ampoules containing a sterile aqueous solution of 16-(3-chlorophenoxy)-1-methoxy-17,18,19,20-tetranor-5-cis,13-trans-prostadien-9α,1-1α,15α-triol, which are used in the manner described in Example 9.

The prostadienoic acid derivative may be replaced by an equivalent amount of another prostadienoic acid of the invention, to give other sterile aqueous solutions.

What we claim is:
1. A prostanoic acid derivative of the formula:

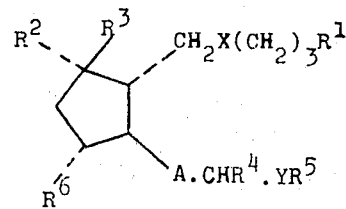

wherein $R^1$ is alkoxymethyl of from 2 to 7 carbon atoms; X is cis-vinylene; $R^2$, $R^4$ and $R^6$ are each hydroxy or alkoxy of 1 to 4 carbon atoms and $R^3$ is hydrogen, or $R^2$ and $R^3$ together are oxo; A is trans-vinylene; Y is alkyleneoxy of 1 to 3 carbon atoms bearing 0, 1 or 2 alkyls of 1 to 3 carbon atoms, and the alkylene of the alkyleneoxy is bonded to the carbon of —$CHR^4$— and the oxygen is bonded to $R^5$; and $R^5$ is phenyl or naphthyl which is unsubstituted or is substituted by chlorine, bromine, fluorine or trifluoromethyl.

2. The prostanoic acid derivative of claim 1 wherein Y is methyleneoxy, or isopropylideneoxy.

3. The prostanoic acid derivative of claim 2 wherein $R^1$ is methoxymethyl or n-butoxymethyl, and Y is methyleneoxy.

4. A prostanoic acid derivative according to claim 1, said derivative being 16-(3-chlorophenoxy)-1-methoxy-17,18,19,20-tetranor-5-cis,13-trans-prostadien-9α,11α,15α-triol.

5. The prostanoic acid derivative of claim 1 which is 1-butoxy-16-(3-chlorophenoxy)-17, 18, 19, 20-tetranor-5-cis, 13-trans-prostadien-9α,11α,15α-triol.

* * * * *